United States Patent [19]

Shim

[11] 4,252,740
[45] Feb. 24, 1981

[54] OXIDATION OF PHENYL PHOSPHONOUS DIHALIDE

[75] Inventor: Kyung S. Shim, Irvington, N.Y.

[73] Assignee: Stauffer Chemical Company, Westport, Conn.

[21] Appl. No.: 946,984

[22] Filed: Sep. 29, 1978

[51] Int. Cl.³ .............................................. C07R 9/42
[52] U.S. Cl. ................................................. 260/543 P
[58] Field of Search ..................................... 260/543 P

[56] References Cited

U.S. PATENT DOCUMENTS

| | | | |
|---|---|---|---|
| 2,683,168 | 7/1954 | Jensen et al. | 260/543 P |
| 2,768,969 | 10/1956 | Isbell et al. | 260/543 P |
| 2,847,469 | 8/1958 | Dawson et al. | 260/543 P |
| 2,870,204 | 1/1959 | Lecher et al. | 260/543 P |
| 2,871,263 | 1/1959 | Short | 260/543 P |
| 2,929,843 | 3/1960 | Dawson et al. | 260/543 P |
| 3,397,122 | 8/1968 | Sennewald et al. | 260/543 P |
| 3,829,480 | 8/1974 | Trescott et al. | 260/543 P |
| 3,897,491 | 7/1975 | Toy et al. | 260/543 P |
| 3,950,413 | 4/1976 | Finke et al. | 260/543 P |

FOREIGN PATENT DOCUMENTS 7020948 1/1972 France ................................. 260/543 P
487083 8/1976 U.S.S.R. .............................. 260/543 P

*Primary Examiner*—Paul J. Killos
*Attorney, Agent, or Firm*—William C. Gerstenzang

[57] ABSTRACT

Phenyl phosphonous dihalide is oxidized according to the following reaction:

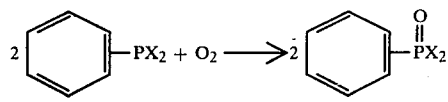

wherein X is Cl or Br.

The reaction is conducted at a temperature from about 0° C. to about 200° C. Charcoal is added to the reaction mixture when impure phenyl phosphonous dihalide is used as a starting material. The product has high purity and is stable at high temperatures. It can be used as an intermediate to prepare flame retardants, insecticides, pesticides and plasticisers.

3 Claims, No Drawings

OXIDATION OF PHENYL PHOSPHONOUS DIHALIDE

BACKGROUND OF THE INVENTION

1. Field of the Invention

The present invention relates to a new and improved method of oxidizing phenyl phosphonous dihalide.

2. The Prior Art

Phenyl phosphonous dihalides are commercially available. Various methods of oxidizing alkyl and aryl phosphonous dihalides have been described in the prior art.

Two methods of oxidizing alkyl phosphonous dihalides are disclosed in U.S. Pat. No. 3,829,480. In that patent a recycle method for oxidizing alkyldihalogenphosphines to the oxides is achieved by the reaction,

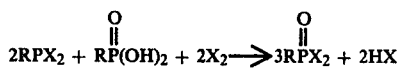

wherein the oxygen donor is prepared by the reaction,

wherein R is any alkyl group and X is any halide. This method yields by-products in contrast to the method of the present invention.

U.S. Pat. No. 3,829,480 also discloses prior art techniques wherein direct oxidation is utilized. According to the patent, however, high pressure and pure starting materials are necessary to carry out such an oxidation process. Accordingly, that direct oxidation method is distinguished from the method of the present invention.

A method of preparing cycloalkane phosphonyl dichlorides is described in U.S. Pat. No. 2,772,308. The method is conducted according to the following reaction scheme:

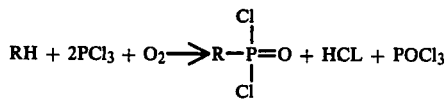

wherein R is a cycloalkane.

SUMMARY OF THE INVENTION

In accordance with the present invention, there is provided a new method of preparing compounds of the formula:

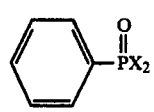

wherein X is Cl or Br.

The compounds are prepared according to the following reaction:

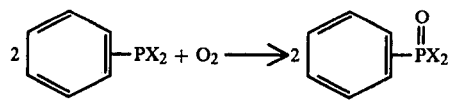

which is conducted at a temperature from about 0° C. to about 200° C. When impure phenylphosphonous dihalide is used as a starting material, charcoal is added to the reaction mixture. The product has high purity and is stable at high temperatures. It can be used as an intermediate to prepare flame retardants, insecticides, pesticides and plasticizers.

DETAILED DESCRIPTION OF THE INVENTION

In the method of the present invention, the phenyl phosphonous dihalide starting material can be used whether it is in the pure form or crude grade. If crude material is utilized, charcoal must be added to the reaction mixture or the reaction will proceed inefficiently if at all. The charcoal is used in amounts from about 0.1% to about 10% by weight of the crude phenyl phosphonous dichloride.

It is a theory of the present invention that the charcoal acts to adsorb impurities that inhibit oxidation (for example, ferric chloride) and to catalyze the reaction. The catalytic effect is believed to occur as a result of the charcoal acting as an oxygen carrier by providing a high surface area for oxygenation.

The reaction can be conducted in any suitable reaction vessel or system capable of holding the starting material. Oxygen can be introduced by bubbling it through the reaction medium or by other suitable means. Constant agitation is necessary to complete the reaction efficiently. The reaction can be conducted batchwise or continuously. When the reaction is completed, any charcoal can be removed by filtration. The product is a clear liquid.

Excess oxygen is utilized to obtain the benzene phosphonic dihalide product.

Temperatures from about 0° C. to about 200° C. can be utilized at atmospheric pressure. There is no particular advantage to heating or pressurizing the reactants.

Reaction times can vary over relatively wide ranges and can easily be determined by one skilled in the art. The primary factor affecting reaction time is the rate of oxygen addition, faster rates of oxygen addition reduce the reaction time. Typical reaction times in a batch system are from about 3 to about 10 hours.

The identification of products is achieved by conventional methods, such as elemental analysis, gas chromatography for purity and mass spectrometer and nuclear magnetic resonance and infra red analysis to establish structure.

The present invention will be more fully illustrated in the examples which follow.

EXAMPLE I

A 300 milliliter, 3 necked flask was fitted with a thermometer, magnetic stirrer, condenser and a glass dispersing tube. Two moles (358 grams) of distilled phenyl phosphonous dichloride was added to the flask followed by addition of benzene phosphinic acid (1 gram) as an impurity. The flask was then placed in a room temperature water bath. Stirring was begun followed by bubbling oxygen through the solution with the dispersing tube at 0.625 moles per hour.

The reaction was conducted over a period of six hours. Starting temperature was 28° C. and a maximum temperature of 52° C. was reached during the reaction. Continuous stirring was maintained for the duration of the reaction. After three and one half hours the water bath was removed. Nine samples were taken over the course of the reaction and were analyzed by gas liquid chromatography. The results are summarized below.

| Sample | Reaction Time | Temperature | % Product |
|---|---|---|---|
| 1 | 0.5 hour | 38° C. | 8.4 |
| 2 | 1.0 | 42 | 18.0 |
| 3 | 1.5 | 48 | 33.6 |
| 4 | 2.0 | 52 | 52.1 |
| 5 | 2.5 | 51 | 67.7 |
| 6 | 3.0 | 42 | 88.6 |
| 7 | 4.0 | 38 | 95.5 |
| 8 | 5.0 | 30 | 96.7 |
| 9 | 6.0 | 28 | 97.0 |

A clear liquid product was produced. The benzene phosphinic acid was not substantially detrimental to the results.

EXAMPLE II

The same equipment was used and procedures were followed as in Example I. Two moles (358 grams) of distilled phenyl phosphonous dichloride were used with benzene phosphonic acid (1 gram) added as an impurity. The results are summarized below.

| Sample | Reaction Time | Temperature | % Product |
|---|---|---|---|
| 1 | 0.5 hour | 36° C. | — |
| 2 | 1.0 | 40 | — |
| 3 | 2.0 | 50 | — |
| 4 | 2.5 | 51 | 34.5 |
| 5 | 3.0 | 49 | 73.6 |
| 6 | 3.5 | 47 | 84.6 |
| 7 | 4.5 | 32 | 94.9 |
| 8 | 5.5 | 28 | 95.1 |

A clear liquid product was produced. The benzene phosphonic acid was not substantially detrimental to the results.

EXAMPLE III

The same equipment was used and procedures were followed as in Example I. Two moles (358 grams) of distilled phenyl phosphonous dichloride were used with water (0.5 grams, distilled) added as an impurity. The results are summarized below.

| Sample | Reaction Time | Temperature | % Product |
|---|---|---|---|
| 1 | 0.5 hour | 34° C. | — |
| 2 | 1.0 | 38 | — |
| 3 | 1.5 | 44 | 15.4 |
| 4 | 2.0 | 50 | 19.1 |
| 5 | 2.5 | 53 | 60.0 |
| 6 | 3.0 | 51 | 73.0 |
| 7 | 4.0 | 39 | 82.1 |
| 8 | 5.0 | 31 | 83.3 |
| 9 | 6.0 | 26 | 93.1 |

A clear liquid product was produced. The water was not substantially detrimental to the results.

EXAMPLE IV

The same equipment was used and procedures were followed as in Example I. Five moles of crude phenyl phosphonous dichloride were used. Oxygen was added at a rate of 1.34 moles per hour. The results are summarized below.

| Sample | Reaction Time | Temperature | % Product |
|---|---|---|---|
| 1 | 0.5 hours | 41° C. | 17.53 |
| 2 | 1.0 | 49 | 36.7 |
| 3 | 1.5 | 55 | 51.9 |
| 4 | 2.0 | 58 | 70.4 |
| 5 | 2.5 | 55 | 81.6 |
| 6 | 3.5 | 52 | 94.2 |
| 7 | 4.5 | 48 | 98.4 |
| 8 | 5.25 | 46 | 99.4 |

Nine hundred and sixty grams of benzene phosphonic dichloride was produced.

EXAMPLE V

The same equipment was used and procedures were followed as in Example I. Crude phenyl phosphonous dichloride (338 grams) having 5% impurities was used. This batch was different from that used in Example IV. Oxygen was added at 15 liters per hour. The results are summarized below.

| Sample | Reaction Time | Temperature | % Product |
|---|---|---|---|
| 1 | 2 hours | 60° C. | 33.0 |
| 2 | 3.75 | 60 | 47.0 |
| 3 | 6 | 42 | 61.4 |

EXAMPLE VI

The same equipment was used and procedures were followed as in Example I. A 311.4 gram portion of crude phenyl phosphonous dichloride was used from the same batch as in Example V. Charcoal (1 gram) was also added to the reaction mixture. Oxygen was added at 13 liters per hour. The results are summarized below.

| Sample | Reaction Time | Temperature | % Product |
|---|---|---|---|
| 1 | 2 hours | 60° C. | 41.4 |
| 2 | 2 | 50 | 79.5 |
| 3 | 6 | 30 | 91 |

The product was then filtered to remove charcoal.

Having set forth the general nature and some examples of the present invention, the scope is now more particularly set forth in the appended claims.

What is claimed is:

1. A method for preparing benzene phosphonic dihalide which comprises reacting benzene phosphonous dihalide with oxygen at a temperature ranging from about 0° C. to about 200° C. and in the presence of charcoal.

2. The method of claim 1 wherein said charcoal is present in an amount ranging from about 0.1 percent to about 10 percent by weight of phosphonous dihalide.

3. The method of claims 1 wherein the benzene phosphonous dihalide is benzene phosphonous dichloride and the benzene phosphonic dihalide is benzene phosphonic dichloride.

* * * * *

UNITED STATES PATENT AND TRADEMARK OFFICE
CERTIFICATE OF CORRECTION

PATENT NO. : 4,252,740
DATED : February 24, 1981
INVENTOR(S) : Kyung S. Shim

It is certified that error appears in the above-identified patent and that said Letters Patent are hereby corrected as shown below:

Col. 4, line 48 (In Table under Reaction Time for Sample 2)
"2" should be -- 4 --.

Signed and Sealed this

Ninth Day of June 1981

[SEAL]

Attest:

RENE D. TEGTMEYER

Attesting Officer     Acting Commissioner of Patents and Trademarks